United States Patent [19]

Maignan et al.

[11] Patent Number: 4,956,175
[45] Date of Patent: Sep. 11, 1990

[54] N-(MERCAPTOALKYL)OMEGA-HYDROXYALKYLAMIDES AND THEIR USE AS A REDUCING AGENT IN A PROCESS FOR PERMANENTLY DEFORMING HAIR

[75] Inventors: Jean Maignan, Tremblay les Gonesse; Gerard Lang, Saint Gratien; Gerard Malle, Villiers sur Morin, all of France

[73] Assignee: Societe Anonyme dite: L'Oreal, Paris, France

[21] Appl. No.: 388,050

[22] Filed: Aug. 2, 1989

[30] Foreign Application Priority Data

Aug. 4, 1988 [LU] Luxembourg .................... 87310

[51] Int. Cl.⁵ .................... A61K 1/09; C07C 235/06
[52] U.S. Cl. .................... 424/72; 424/71; 564/201; 564/192
[58] Field of Search .................... 564/201, 203; 514/625; 424/72

[56] References Cited

U.S. PATENT DOCUMENTS

| 2,170,845 | 8/1939 | Woodhouse | 564/203 |
|---|---|---|---|
| 2,368,073 | 1/1945 | Tryon | 564/203 |
| 2,813,123 | 11/1957 | Valentine et al. | 564/203 |
| 2,923,738 | 2/1960 | Williams et al. | 564/201 |
| 3,230,228 | 1/1966 | Erlemann et al. | 564/201 |
| 3,840,656 | 10/1974 | Kalopissis et al. | 424/72 |
| 3,849,576 | 11/1974 | Kalopissis | 424/72 |
| 4,448,905 | 5/1984 | Lin et al. | 564/203 |

FOREIGN PATENT DOCUMENTS

| 2587030 | 3/1987 | France | 564/201 |
|---|---|---|---|
| 0260058 | 11/1986 | Japan | 564/201 |

*Primary Examiner*—Richard L. Raymond
*Assistant Examiner*—Susan P. Treanor
*Attorney, Agent, or Firm*—Cushman, Darby & Cushman

[57] ABSTRACT

An N-(mercaptoalkyl)ω-hydroxyalkylamide having the formula,

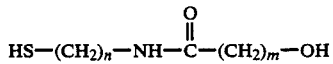

wherein n is 2 or 3 and m is 2 to 5 inclusive is employed as a reducing agent in the first stage reducing operation of permanently deforming hair.

8 Claims, No Drawings

N-(MERCAPTOALKYL)OMEGA-HYDROXYALKYLAMIDES AND THEIR USE AS A REDUCING AGENT IN A PROCESS FOR PERMANENTLY DEFORMING HAIR

The present invention relates to new N-(mercaptoalkyl)ω-hydroxyalkylamides and their use, as reducing agents, in the permanent deformation of hair.

The technique of effecting a permanent deformation of hair comprises, in a first stage, the opening of the disulfide bonds of keratin (cystine) using a composition containing a reducing agent (reducing stage), then preferably after having rinsed the hair, reconstituting, in a second stage, the said disulfide bonds by applying to the hair, under tension, an oxidizing composition (oxidation stage, also called a fixation stage), so as to give the desired form to the hair. This technique permits indifferently, to effect either waving the hair, or uncurling or uncrisping the hair.

Compositions to effect the first stage of a permanent waving operating are generally provided in the form of lotions, creams, gels or powders to be diluted in a liquid support and contain, preferably, a mercaptan as the reducing agent.

Among these latter, those currently employed are thioglycolic acid and thiolactic acid or a mixture of these acids, as well as their esters, for example, the monothioglycolate of glycerol or glycol.

These reducing agents which are particularly effective in reducing the disulfide bonds of keratin include, principally, thioglycolic acid which can be considered as the product of choice in permanent waving operations. It provides a reduction in the amount of about 50%.

These reducing agents exhibit, however, a major disadvantage since they emit bad odors, characteristic of sulfur compounds, which at times render the permanent waving operation distressing, not only for persons who undergo such an operation, but also for persons effecting such an operation.

With a view to reducing this disadvantage, a perfume is generally employed to mask the odors.

Moreover, studies have been conducted with a view to perfecting new odorless reducing agents. Thus, in Japanese patent application (Kokai) No. 260.058/86, the use of N-mercaptoalkylgluconamides, which are water-soluble compounds, having weak volatility and practically odor free, have been proposed.

These N-mercaptoalkylgluconamides are obtained by reaction of glucono-δ-lactone with an aminoalkanethiol.

These new reducing agents, if they provide a remedy for the disadvantages of known reducing agents, they do not possess however the excellent reducing properties enjoyed principally by thioglycolic acid.

It has now been noted, in a quite surprising fashion, that by employing a new class of mercaptoalkylamides, principally N-(mercaptoalkyl)ω-hydroxyalkylamides, it is possible to remedy the disadvantages of these various reducing agents.

The N-(mercaptoalkyl)ω-hydroxyalkylamides, according to the present invention, exhibit excellent reducing properties which are quite comparable to those of thioglycolic acid but importantly they are odor fee.

The present invention relates to, as a new industrial product, water soluble N-(mercaptoalkyl)ω-hydroxyalkylamides, having the formula $$HS-(CH_2)_n-NH-\overset{O}{\underset{\|}{C}}-(CH_2)_m-OH \quad (I)$$

wherein
n is 2 or 3, and
m is 2 to 5 inclusive.

In accordance with a preferred embodiment of the present invention, n is 2 and m is 3 or 4.

Representative N-(mercaptoalkyl)ω-hydroxyalkylamides of formula (I) above, include principally the following:
4-hydroxy N-(2-mercaptoalkyl) butyramide,
3-hydroxy N-(2-mercaptoethyl) propionamide,
5-hydroxy N-(2-mercaptoethyl) valeramide,
4-hydroxy N-(3-mercaptopropyl) butyramide,
6-hydroxy N-(2-mercaptoethyl) caproamide and
6-hydroxy N-(3-mercaptopropyl) caproamide.

Among these, 4-hydroxy N-(2-mercaptoethyl) butyramide is particularly preferred.

The present invention also relates to a process for preparing the mercaptoalkylamides in accordance with the invention, this process comprising reacting a mercaptoalkylamine (1) with a lactone (2) in accordance with the following reaction scheme:

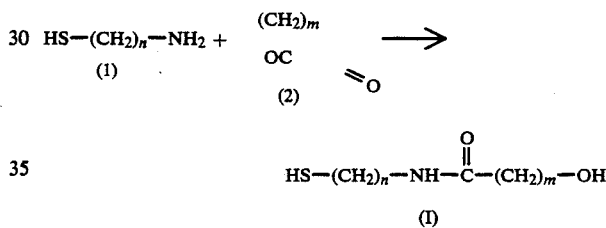

The mercaptoalkylamines (1) employed are either 2-mercaptoethylamine or cysteamine (n=2) or 3-mercaptopropylamine (n=3).

The lactones (2) are β-propionolactone (m=2), γ-butyrolactone (m=3), valerolactone (m=4) or caprolactone (m=5).

The reaction of opening the lactone is generally carried out under an inert atmosphere in an alcohol such as methanol, ethanol, isopropanol or butanol, and depending on the boiling point of the latter, at a temperature between 20° and 110° C.

The reaction time is generally long and can require several days so that it can be advantageous not to employ a solvent and to mix the mercaptoalkylamine and the lactone in stoichiometric proportions and to bring the mixture to a temperature between 20° and 80° C.

The evolution of the reaction is followed by dosage of the non-transformed mercaptoalkylamine. When the reaction time is too long, an excess of mercaptoalkylamine can advantageously be employed and the excess is removed at the end of the reaction by filtering the mixture on a sulfonic acid resin.

If, during the course of the reaction, a certain amount of thiol is oxidized to the corresponding disulfide, the reaction mixture is then diluted by twice its volume with water and stirred in the presence of a mixture of sulfonic resin and zinc powder for 3 to 10 hours.

The majority of the disulfide being reduced, the mixture is then filtered, thus resulting in a solution of the expected compound which can be used directly.

In accordance with a preferred embodiment of the process of the present invention, the mercaptoalkylamines can be employed in the hydrochloride form considered as the primary material, the free amine being liberated by the triethanolamine. In this case, after the end of the reaction the expected compound is obtained with an equivalent of triethanolamine hydrochloride whose presence does not modify the properties of the N-(mercaptoalkyl)ω-hydroxyalkylamides of the present invention.

It can be advantageous to operate in an autoclave which eliminates sublimation problems of the cysteamine.

The present invention also relates to, as a new industrial product, the disulfides of the compounds of formula (I) which can be represented by the formula

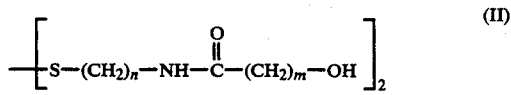

wherein
n and m have the same meanings as those given above for formula (I).

The disulfides are usefully employed in compositions called "self-neutralizers", i.e., they are combined with a thiol, such as for example an N-(mercaptoalkyl)ω-hydroxyalkylamide of formula (I) above, in molar amounts ranging from 0.5 to 2.5 and preferably from 1 to 2 (see U.S. Pat. No. 3,768,490).

The disulfides of formula (II) in accordance with the present invention are obtained by oxidizing the compounds of formula (I) either in air or by using, for example, $H_2O_2$ in the optional presence of ferrous ions.

They can also be obtained by reacting a disulfide of formula (3) with a lactone (2) in accordance with the following reaction scheme:

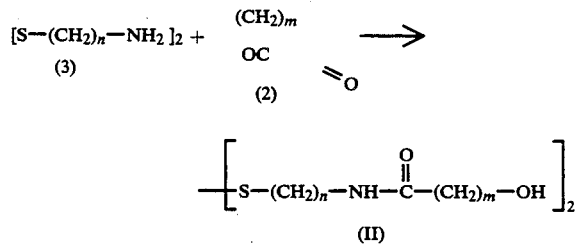

Representative disulfides of formula (II) above include, principally, the following:
  bis (N-4-ethylhydroxy butyramide) disulfide,
  bis (N-5-ethylhydroxy valeramide) disulfide,
  bis (N-6-ethylhydroxy caproamide) disulfide,
  bis (N-3-hydroxyethyl propionamide) disulfide,
  bis (N-4-hydroxypropyl butyramide) disulfide and
  bis (N-6-hydroxypropyl caproamide) disulfide.

The present invention also relates to a reducing composition, for the first stage of a permanent deformation operation of hair comprising, in a cosmetically acceptable vehicle, at least one N-(mercaptoalkyl)ω-hydroxyalkylamide of formula (I) such as defined above, as the reducing agent.

Preferably, the reducing agent is present in the composition according to the invention in an amount between 2 and 20 weight percent and, preferably, between 5 and 10 weight percent relative to the total weight of the reducing composition.

The pH of the composition is generally between 6.5 and 10 and is obtained using an alkaline agent such as, for example, ammonia, monoethanolamine, diethanolamine, triethanolamine, an alkaline or ammonium carbonate or bicarbonate.

The reducing composition can also contain various ingredients such as, for example, cationic polymers such as those employed in the compositions of French Pat. Nos. 79.32078 and 80.26421 or even cationic polymers of the ionene type, such as those used in the compositions of French Pat. No. 82.17364, softening agents and principally quaternary ammonium derivatives of lanolin, protein hydrolyzates, waxes, opacifying agents, perfumes, dyes, non-ionic or cationic surface active agents, treating agents or even penetration agents such as urea, pyrrolidone or thiomorpholinone.

The reducing composition according to the invention can also be of the exothermic type, i.e., provoking a certain amount of heat during application to the hair, which is agreeable to the person undergoing the first stage of the permanent or uncurling of the hair.

The vehicle of the compositions according to the invention is preferably water or a hydroalcoholic solution of a lower alcohol such as ethanol, isopropanol or butanol.

When the compositions are intended for a hair uncurling or uncrisping operation, the reducing composition is preferably in the form of a cream so as to maintain the hair as rigid or stiff as possible. These creams are provided in the form of "heavy" emulsions, for example, those based on glyceryl stearate, glycol stearate, self-emulsifying waxes, fatty alcohols, etc. Liquids or gels containing thickening agents, such as carboxyvinyl polymers or copolymers which "glue" the hair can also be employed so as to maintain the hair in a smooth position during the setting period.

The present invention also relates to a hair waving process comprising applying a reducing composition, such as defined above, to wet hair previously rolled on rollers which have a diameter of 4 to 20 mm. The composition can optionally be applied gradually on rolling the hair.

The reducing composition is then permitted to act on the hair for a period of time ranging from 5 to 60 minutes and preferably 5 to 30 minutes. The hair is then thoroughly rinsed after which there is applied to the rolled up hair, an oxidizing composition so as to reform the disulfide bonds of the keratin during a setting period of 2 to 10 minutes. After having removed the rollers the hair is thoroughly rinsed.

The oxidation composition, or oxidizing agent, is of the type currently employed and contains as the oxidizing agent $H_2O_2$, an alkaline bromate, a per salt or a mixture of an alkaline bromate and a per salt. The concentration of $H_2O_2$ can vary from 3 to 10 volumes; the concentration of alkaline bromate, from 2 to 12 weight percent and that of the per salt from 0.1 to 15 weight percent based on the total weight of the oxidation composition.

The present invention also relates to a process for uncurling or uncrisping the hair which comprises applying to the hair a reducing composition, according to the invention, submitting the hair to a mechanical deformation so as to fix the hair in a new form, by smoothing the hair with a comb having large teeth or with the back of the comb or with the hand. After a setting period of 5 to 60 minutes, particularly 5 to 30 minutes, the hair is again smoothed and then carefully rinsed. The oxidation or fixing composition is then applied to the hair and left in contact therewith for about 2 to 10 minutes. The hair is then thoroughly rinsed.

There are now given, as an illustration and without any limiting character, several examples of preparing the N-(mercaptoalkyl)ω-hydroxyalkylamides and their disulfides, as well as several examples of compositions containing them.

EXAMPLE I

Preparation of 4-hydroxy N-(2-mercaptoethyl)butyramide (a) Reaction carried out at 80° C. starting with cysteamine In a reactor, a mixture of 15.2 g of cysteamine and 15 cm³ of γ-butyrolactone is stirred under an inert atmosphere for 5 hours at a temperature of about 80° C. The disappearance of the γ-butyrolactone is followed by vapor phase chromatography (VPC).

When the γ-butyrolactone is no longer detected in the reaction mixture, the latter is poured into 100 cm³ of water to which are added 10 g of sulfonic resin, "Dowex 50" (partially hydrated at 45%) and 5 g of zinc powder so as to reduce the small amount of disulfide being formed during the course of the reaction. The whole is stirred for two hours at ambient temperature and then filtered under an inert atmosphere. A perfectly colorless aqueous solution is obtained. It is evaporated under reduced pressure and 25 g of 4-hydroxy N-(2-mercaptoethyl) butyramide are obtained.

It is a colorless liquid at ambient temperature.

The NMR[1]H 80 MHz conforms to the expected structure.

The thiol dosage in an acid medium is 95% and the elemental analysis corresponds to a partially hydrated product: $C_6H_{13}NO_2S \cdot \frac{1}{2}H_2O$

|  | C | H | N | O | S |
|---|---|---|---|---|---|
| Calculated | 41.84 | 8.19 | 8.13 | 23.22 | 18.62 |
| Found | 41.59 | 7.83 | 8.56 | 22.84 | 18.85 |

(b) Reaction carried out at ambient temperature starting with cysteamine

In a round bottom flask, 7.72 g of cysteamine and 8.61 g of γ-butyrolactone under an inert atmosphere are mixed. The mixture thus obtained is stirred for 10 days at ambient temperature. The initially pasty medium progressively becomes homogeneous so as to give a clear and relatively mobile liquid. The total transformation of the γ-butyrolactone is verified at this stage by VPC and that of the cysteamine by dosage with perchloric acid. The dosage of the thiol is 100%.

15 g of 4-hydroxy N-(2-mercaptoethyl) butyramide are obtained.

(c) Reaction carried out starting with cysteamine hydrochloride

In a reactor there are introduced, at ambient temperature and under an inert atmosphere, 11.4 g of cysteamine hydrochloride and then slowly, with stirring, 13.5 cm³ of triethanolamine. To the resulting mixture, brought to a temperature of about 60° C., 7.7 cm³ of γ-butyrolactone are slowly added. At the end of the introduction the whole is brought to a temperature of 90° C. for three hours, at the end of which time all the γ-butyrolactone is transformed (VPC verification). 32 g of 4-hydroxy N-(2-mercaptoethyl) butyramide are obtained containing one equivalent of triethanolamine hydrochloride in the form of a pasty white solid that is conditioned under an inert atmosphere.

The dosages correspond to the expected mixture.

(d) Reaction carried out starting with cysteamine hydrochloride with removal of the triethanolamine hydrochloride formed Into a reactor, fitted with a mechanical stirrer, 228 g of cysteamine hydrochloride are introduced and are placed under an argon atmosphere. 270 cm³ of triethanolamine are slowly added, with stirring, over a period of about 1 hour 30 minutes. The pasty reaction mixture is then brought to 60° C. and, at this temperature, 155 cm³ of γ-butyrolactone are slowly introduced. At the end of the addition, the whole is then brought for 8 hours at 80° C., at the end of which time all the γ-butyrolactone is transformed. 305 cm³ of absolute ethanol are then introduced and stirring is maintained at 60° C. for one-half hour.

The mixture is then cooled to about 15° C. and the triethanolamine hydrochloride is filtered. The filtrate is concentrated under reduced pressure to remove the ethanol.

250 g of 4-hydroxy N-(2-mercaptoethyl) butyramide are obtained.

EXAMPLE II

Preparation of 5-hydroxy N-(2-mercaptoethyl) valeramide

A mixture, stirred under an inert atmosphere, of 5 g of cysteamine and 6.05 cm³ of δ-valerolactone is brought to a temperature of about 60°-70° C. for 15 hours. The disappearance of the δ-valerolactone is followed by VPC. The reaction mixture is then poured into 100 cm³ of water and 10 g of acid resin, "Dowex 50" and 3 g of zinc powder are added. The resulting mixture is stirred for 4 hours at ambient temperature and then left overnight. The next day the mixture is filtered and the water is evaporated under reduced pressure.

There are thus obtained 8 g of 5-hydroxy N-(2-mercaptoethyl) valeramide in the form of a colorless liquid whose NMR[1]H spectrum, as well as the thiol dosages and residual amine, conform to the expected structure.

EXAMPLE III

Preparation of 6-hydroxy N-(2-mercaptoethyl) caproamide

A mixture, under an inert atmosphere, of 5 g of cysteamine and 7.2 cm³ of ε-caprolactone is stirred for 6 hours at ambient temperature. It is then left to stand overnight, after which the mixture is heated for 4 hours at a temperature of about 60° C. At the end of this time all the ε-caprolactone is transformed. The mixture is then poured into 100 cm³ of water to which 10 g of acid resin, "Dowex 50" are added and then 3 g of powdered zinc. The whole is stirred for 4 hours at ambient temperature. The water is then removed under reduced pressure and there are obtained 10 g of 6-hydroxy N-(2-mercaptoethyl) caproamide in the form of a viscous liquid at ambient temperature whose NMR[1]H spectrum and thiol dosages and residual amine correspond to the expected structure.

EXAMPLE IV

Preparation of bis (N-4-ethylhydroxy butyramide) disulfide

First Method

A solution of 20 g of 4-hydroxy N-(2-mercaptoethyl) butyramide in 300 cm³ of anhydrous ethanol is stirred in air in the presence of 20 cm³ of triethylamine for 48 hours at the end of which time the thiol is transformed into the corresponding disulfide. The solvent and the triethylamine are removed by evaporation under a vacuum.

The resulting pasty product is finely divided by stirring in methylene chloride, filtered and then recrystallized in 200 cm³ of acetonitrile.

15 g of bis (N-4-ethylhydroxy butyramide) disulfide in the form of white crystals whose melting point is 102° C. are obtained.

| Elemental analysis: $C_{12}H_{24}N_2O_4S_2$ | | | | | |
| --- | --- | --- | --- | --- | --- |
| | C | H | N | O | S |
| Calculated | 44.42 | 7.47 | 8.64 | 19.72 | 19.76 |
| Found | 44.55 | 7.51 | 8.47 | 20.02 | 19.67 |

Second Method

Into a reactor there are introduced, successively and at ambient temperature, 11.26 g (0.05 mole) of cysteamine hydrochloride, 14.92 g (0.1 mole) of triethanolamine, 8.61 g (0.1 mole) of γ-butyrolactone and finally 20 cm³ of absolute ethanol. The resulting mixture is brought for 4 hours to 80° C.

The reaction mixture is then filtered on fritted glass. The solid and the filtrate are separately treated.

The solid is taken up in 75 cm³ of boiling acetonitrile. The insolubles are removed by filtration and the filtrate provides, on cooling, 8.3 g of a white solid.

The filtrate is evaporated to dryness and then taken up with 30 cm³ of boiling acetonitrile. The insolubles are removed on fritted glass and the filtrate gives, on cooling, 2.4 g of a white solid.

A total of 10.7 g of bis (N-4-ethylhydroxy butyramide) disulfide having a melting point of 98°-100° C. are obtained.

The NMR[1]H 80 MHz spectrum conforms to the expected structure.

In accordance with the same operating procedures described above the other disulfides mentioned above have been obtained.

EXAMPLE V

Preparation of bis (N-5-ethylhydroxy valeramide) disulfide

To a solution of 1.77 g (0.1 mole) of 5-hydroxy N-(2-mercaptoethyl) valeramide in 20 cm³ of absolute alcohol, cooled to +5° C., 4.6 cm³ (0.045 mole) of 30% $H_2O_2$ are slowly added.

Stirring is then maintained for 1 hour while letting the temperature return to ambient temperature. The thiol dosage is negative. The reaction medium is then evaporated to dryness under reduced pressure. After prolonged drying under a vacuum at ambient temperature, 1.5 g of bis (N-5-ethylhydroxy valeramide) disulfide are obtained which slowly crystallizes under the form of a white waxy solid.

The NMR[1]H 80 MHz spectrum conforms to the expected structure.

EXAMPLE VI

Preparation of bis (N-6-ethylhydroxy caproamide) disulfide

To a solution of 1.92 g (0.1 mole) of 6-hydroxy N-(2-mercaptoethyl) caproamide in 20 cm³ of ethanol, cooled to +5° C., 5.0 cm³ (0.049 mole) of 30% $H_2O_2$ are slowly added with stirring. After 2 hours of stirring at ambient temperature (thiol test negative) the solution is clarified by paper filtration and then evaporated to dryness under reduced pressure. After prolonged drying under a vacuum at ambient temperature 1.7 g of bis (N-6-ethylhydroxy caproamide) disulfide in the form of a thick pale yellow gel are obtained.

The NMR[1] 80 MHz spectrum conforms to the expected structure.

Composition Examples

I - In accordance with the invention, a permanent deformation reducing composition for hair is prepared by admixing the following ingredients:

| | |
| --- | --- |
| 4-hydroxy N-(2-mercaptoethyl butyramide | 9 g |
| Ammonia, sufficient amount for pH = 9 | |
| Perfume | 0.1 g |
| Preservative | 0.5 g |
| Demineralized water, sufficient amount for | 100 g |

This composition is applied to moistened hair, previously rolled on hair setting rollers. After permitting the composition to act for about 15 minutes the hair is thoroughly rinsed with water. The following oxidation composition is then applied to the hair:

| | |
| --- | --- |
| $H_2O_2$, sufficient amount for | 8 volumes |
| Stabilizer | 0.3 g |
| Perfume | 0.1 g |
| Lactic acid, sufficient amount for pH = 3 | |
| Demineralized water, sufficient amount for | 100 g |

The oxidizing composition is permitted to act on the hair for about 10 minutes. The rollers are removed and the hair is thoroughly rinsed with water.

After drying under a hood the hair exhibits beautiful curls.

In this example the reducing composition can advantageously be replaced by one of the following reducing compositions:

| | | |
| --- | --- | --- |
| (A) | 4-hydroxy N-(2-mercaptoethyl butyramide) | 12 g |
| | Monoethanolamine, sufficient amount for pH = 9 | |
| | Perfume | 0.1 g |
| | Preservative | 0.5 g |
| | Demineralized water, sufficient amount for | 100 g |
| (B) | 5-hydroxy N-(2-mercaptoethyl) valeramide | 10 g |
| | Monoethanolamine, sufficient amount for pH = 8.5 | |
| | Perfume | 0.1 g |
| | Preservative | 0.5 g |
| | Demineralized water, sufficient amount for | 100 g |
| (C) | 6-hydroxy N-(2-mercaptoethyl) caproamide | 7 g |
| | Ammonia, sufficient amount for pH = 8.5 | |
| | Perfume | 0.1 g |
| | Preservative | 0.5 g |
| | Demineralized water, sufficient amount for | 100 g |

II In accordance with the invention, a composition is prepared to effect a "self-neutralizing" permanent by admixing the following components:

| | |
|---|---|
| 4-hydroxy N-(2-mercaptoethyl) butyramide | 6.3 g |
| Bis (N-4-ethylhydroxy butyramide) disulfide | 17.5 g |
| Urea | 8 g |
| Perfume | 0.1 g |
| Preservative | 0.5 g |
| Ammonia, sufficient amount for pH = 9.5 | |
| Water, sufficient amount for | 100 g |

This solution is applied to moistened hair, previously rolled up on hair setting rollers and is permitted to remain in contact with the hair for about 20 minutes. The rollers are removed and the hair is thoroughly rinsed with water.

After drying under a hood the hair exhibits beautiful waves.

What is claimed is:

1. N-(mercaptoalkyl)ω-hydroxyalkylamide having the formula

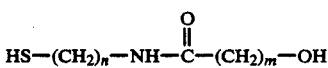 (I)

wherein
n is 2 or 3, and
m is 2 to 5 inclusive.

2. The compound of claim 1 wherein n is 2 and m is 3 or 4.

3. The compound of claim 1 selected from
4-hydroxy N-(2-mercaptoethyl) butyramide,
3-hydroxy N-(2-mercaptoethyl) propionamide,
5-hydroxy N-(2-mercaptoethyl) valeramide,
4-hydroxy N-(3-mercaptopropyl) butyramide,
6-hydroxy N-(2-mercaptoethyl) caproamide, and
6-hydroxy N-(3-mercaptopropyl) caproamide.

4. A cosmetic reducing composition for the first stage of a permanent deformation operation for hair, comprising in a cosmetically acceptable vehicle, as a reducing agent, at least one N-(mercaptoalkyl)ω-hydroxyalkylamide of claim 1.

5. The cosmetic reducing composition of claim 4 wherein said reducing agent is present in an amount ranging from 2 to 20 weight percent based on the total weight of said composition.

6. The cosmetic reducing composition of claim 4 wherein said reducing agent is present in an amount ranging from 5 to 10 weight percent based on the total weight of said composition.

7. The cosmetic reducing composition of claim 4 having a pH between 6.5 and 10.

8. The cosmetic reducing composition of claim 4 which also includes at least one of a cationic polymer, a softening agent, a protein hydrolyzate, a wax, an opacifying agent, a perfume, a dye, a non-ionic or cationic surface active agent, a treating agent or a penetration agent.

* * * * *